US00PP09091P

United States Patent [19]

Vinson et al.

[11] Patent Number: Plant 9,091

[45] Date of Patent: Mar. 28, 1995

[54] STRAWBERRY PLANT—EVITA VARIETY

[75] Inventors: Peter E. Vinson; Simon P. Warren, both of Kent, United Kingdom

[73] Assignee: Edward Vinson Limited, Kent, United Kingdom

[21] Appl. No.: 183,980

[22] Filed: Jan. 21, 1994

[51] Int. Cl.[6] ..... A01H 5/00

[52] U.S. Cl. ..... Plt./49

[58] Field of Search ..... Plt. 49

*Primary Examiner*—James R. Feyrer

*Attorney, Agent, or Firm*—Burns, Doane, Swecker & Mathis

[57] ABSTRACT

A new and distinct variety of everbearing strawberry plant is provided which originated as a cross between the Chandler variety (U.S. Plant Pat. No. 5,262) and an unnamed seedling designated B144. The new variety is self-pollinating and generally forms flowers that are clear of the foliage and tend to protrude primarily to the side of the plant. The large berries are of a glossy fully-colored bright orange-red coloration and are primarily conical in configuration and sometimes are wedge-shaped. The flesh of the new variety is firm and possesses a good combination of flavor, sugars, and acidity. To date a high level of tolerance to strawberry mildew has been exhibited by the new variety.

3 Drawing Sheets

SUMMARY OF THE INVENTION

The new variety of strawberry plant (*Fragaria*×*Ananassa*) of the present invention is the product of a planned breeding program carried out at property of Edward Vinson Limited located at Sandbanks Farm, Faversham, Kent, ME13 9DJ, United Kingdom. The cross was carried out during 1988, and the initial selection was made during 1990 following observation of the first fruiting during 1989. The female parent (i.e., the seed parent) was the Chandler variety developed at the University of California (U.S. Plant Pat. No. 5,262), and the male parent (i.e., the pollen parent) was an unnamed seedling designated B144 (non-patented in the United States). The B144 plant was formed by the crossing of the short-day Gorella variety (non-patented in the United States) by the day-neutral Brighton variety developed at the University of California (U.S. Plant Pat. No. 4,489). The new variety of the present invention was found to be day-neutral and initially was designated 89A24.

It was found that the new strawberry variety of the present invention possesses the following combination of characteristics:

(a) exhibits a semi-erect growth habit,
(b) is self-pollinating and tends to bear flowers that are clear of the foliage and which protrude primarily to the sides of the plant,
(c) bears leaflets having a slightly-rounded base and slightly-rounded serrations wherein the leaflets commonly tend to be slightly longer in length than in width, and
(d) forms on an everbearing basis medium to large attractive berries that exhibit a glossy fully-colored bright orange-red appearance that primarily are conical and sometimes are wedge-shaped in configuration.

To date the foliage and berries of the new strawberry variety have demonstrated a high level of tolerance to strawberry mildew (i.e., *Sphaerotheca macularis*).

The new strawberry variety has been found to behave in a manner similar to that of day-neutral cultivars, such as Brighton (U.S. Plant Pat. No. 4,489) and Selva (U.S. Plant Pat. No. 5,266), that were developed at the University of California. More specifically, the new variety of the present invention will flower and fruit on an everbearing basis that is believed to be independent of the day length. Also, it has been observed that exposure to high temperatures does not cause the plant to enter a non-fruiting phase. Unlike the Fern variety (U.S. Plant Pat. No. 5,267), the new variety of the present invention continues to produce flowers and to bear throughout the season as cycles of flower production. The flowers of the new variety are self-fertile and tend to form an abundance of pollen. This generally has yield fruits of good shape with little malformation of the berry crop.

The new variety has been asexually reproduced by runners at Edward Vinson Limited, Sandbanks, Graveney, Faversham, Kent, ME13 9DJ, United Kingdom. The characteristics of the new variety are stably transmitted from one generation to another using asexual propagation by runners. Fewer runners are produced per mother plant of the new variety than are formed on the Selva variety (U.S. Plant Pat. No. 5,266). However, the runners which are formed tend to be strong and to exhibit a good propensity to flower and fruit.

The new variety has been tested at Brogdale Trust, Brogdale Farm, Faversham, Kent, United Kingdom, and at the Horticultural Research International Testing Station, Efford, Lymington, Hampshire, United Kingdom. Wider scale testing also has been conducted on mainland Europe.

The Evita name has been selected for the new variety.

BRIEF DESCRIPTION OF THE PHOTOGRAPHS

The accomapnying photographs show typical specimens of the variety and the fruit thereof as depicted in color as nearly true as it is reasonably possible to make the same in color illustrations of this character. The plants illustrated were being grown at planting areas of Edward Vinson Limited, Kent, United Kingdom. The photograph of FIG. 1 was obtained during early summer, and the photographs of FIGS. 2, 3, and 4 were obtained during mid-summer.

DETAILED DESCRIPTION

Figure 1:
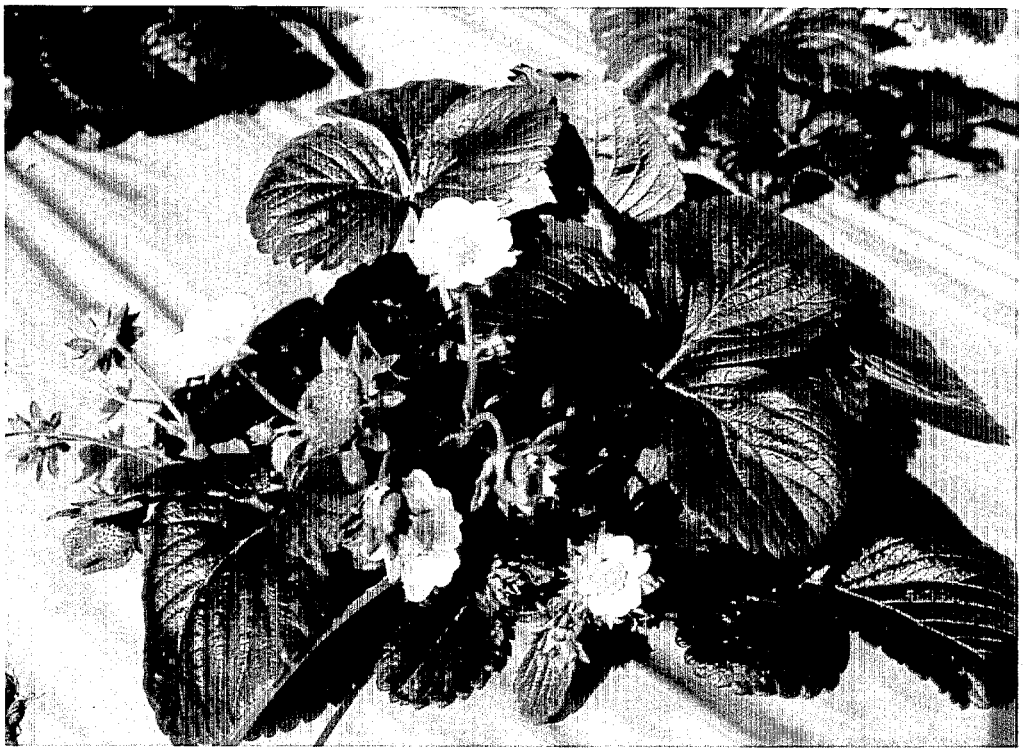
FIG. 1 shows the typical semi-erect growth habit, flowers, and the appearance of the immature berries and leaves of the new Evita variety.
Figure 2:
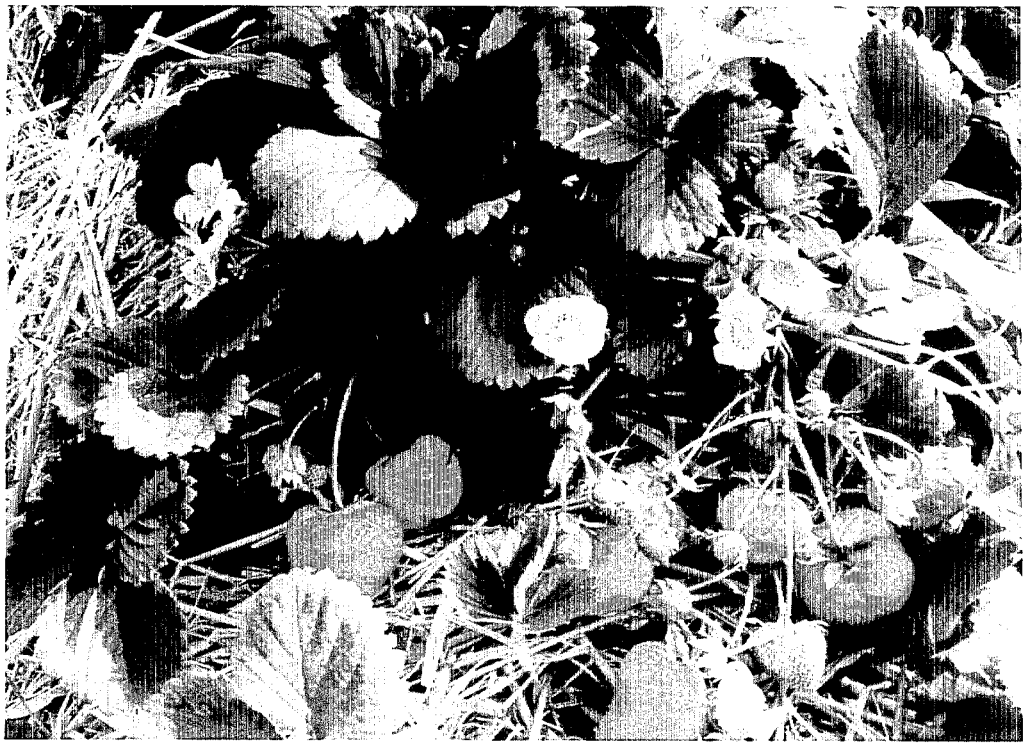
FIG. 2 shows typical mature leaves, and immature and mature berries of the new Evita variety.
Figure 3:
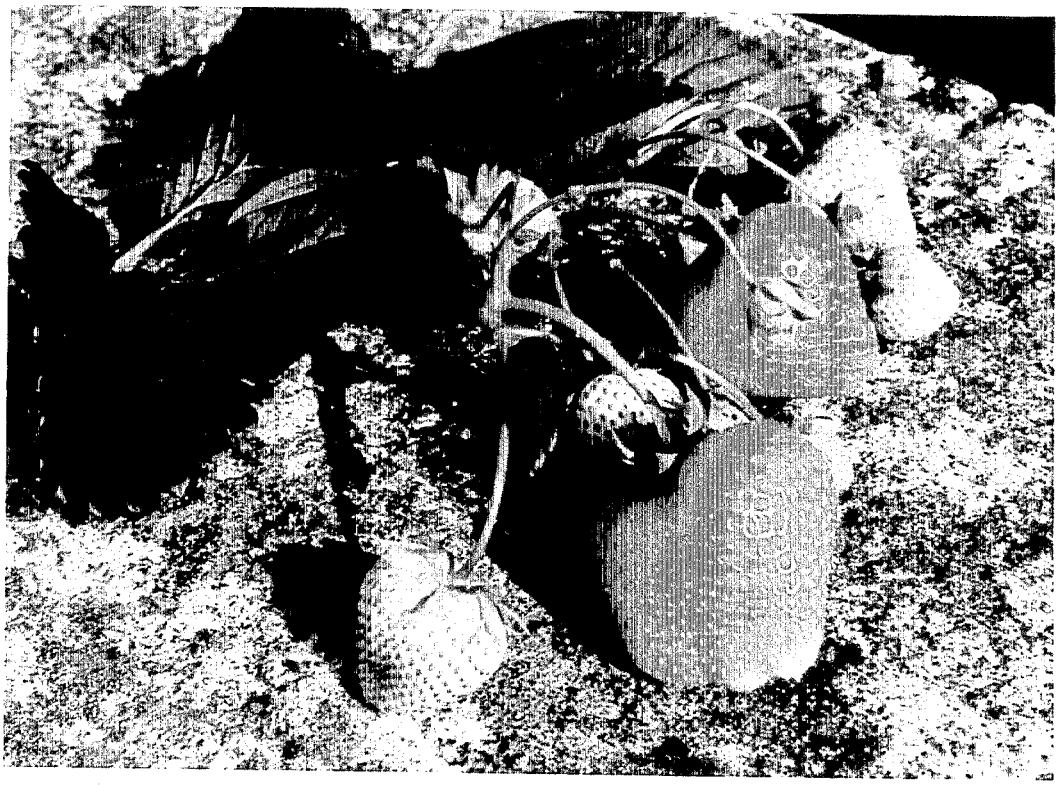
FIG. 3 shows typical mature leaves and a bright and glossy mature berry of the new Evita variety.

The following is a detailed description of the new Evita strawberry variety. The specimens described had been asexually reproduced from runners and were grown at property of Edward Vinson Limited, Sandbanks, Graveney, Faversham, Kent, ME13 9DJ, United Kingdom. Color designations are presented hereafter with reference to The R.H.S. Colour Chart of The Royal Horticultural Society, London, England.

Plant and Foliage

The new Evita variety exhibits a semi-erect somewhat open growth habit, and when grown in the United Kingdom assumes a plant size that is generally comparable to that of the Selva variety (U.S. Plant Pat. No. 5,266). The leaf coloration of the new variety is slightly paler than that of the Selva variety when grown under the same conditions. The leaflets generally are somewhat longer than they are wide, and tend to possess a slightly round base and slightly rounded serrations. The petiole hairs tend to extend outwardly from the leaf stalk in a generally perpendicular disposition.

The coloration of upper leaf surfaces commonly ranges from Yellow-Green Group 146A to 147A, and the coloration of the under leaf surfaces commonly approaches Green Group 138B. When grown in South East England, a very slight yellow-green inter-veinal mottling commonly is observable on some but not all of the upper leaf surfaces. The very slight mottling tends not to be observable in photographs and tends to be more prevalent on younger leaves than on mature leaves. There is no significant leaf coloration change throughout the growing season. As indicated, the individual leaves typically are longer in length than in width and commonly range from approximately 6 cm in length×approximately 5 cm in width to approximately 10 cm in length×approximately 8 cm in width with most leaves commonly measuring approximately 9 cm in length×approximately 7 cm in width. The typical margin serration count is approximately 1.3 to 1.4 per cm.

The leaf pedicels commonly average approximately 22 mm in length, and their coloration commonly approaches that of Yellow-Green Group 145B. Pointed stipules commonly are present.

A mature plant of the new variety at the beginning of August when grown at the indicated location commonly measures approximately 20 cm in height and approximately 40 cm in width.

Flowering and Fruiting

When grown under European growing conditions, the new variety is everbearing and flowers and fruits in a manner similar to that of the Brighton and Selva varieties that is independent of the day length. Extremely high temperatures have not been observed to cause the new variety to enter a phase in which fruit production ceases. The flower trusses tend to be borne clear of the foliage canopy and generally to protrude to the sides of the plant rather than in a totally upwards direction. The flowers tend to be strong and generally are fewer in number than those formed on the Rapella everbearing strawberry variety (non-patented in the United States). The flowers have been observed to form ample pollen and readily to undergo self-pollination. When grown at Kent, United Kingdom, the Evita variety commonly commences fruiting about ten weeks following the mid-April planting date. Little data is available concerning the flowering of the new variety when grown in warmer climates; however, when freshly dug runners were planted in Spain at the beginning of October, flowers were observed approximately six weeks thereafter.

Replicated trails at South East England have shown that the new Evita variety typically produces berry yields that are equal to or greater than those of the Rapella variety. The cropping pattern for the Evita variety tends to be regular in the absence of flushes, and is very similar to that of the Rappela variety. A berry crop using day neutral types is commonly produced from July to October in South East England.

The chilling requirements of the new variety have not been fully evaluated since the growing conditions in South East England are not dependent on artificial chill conditions. The new variety has performed well when exposed to the ambient normal winter chill and also when grown from tissue culture plants that have received no chill.

Fruit Appearance and Quality

Figure 4:
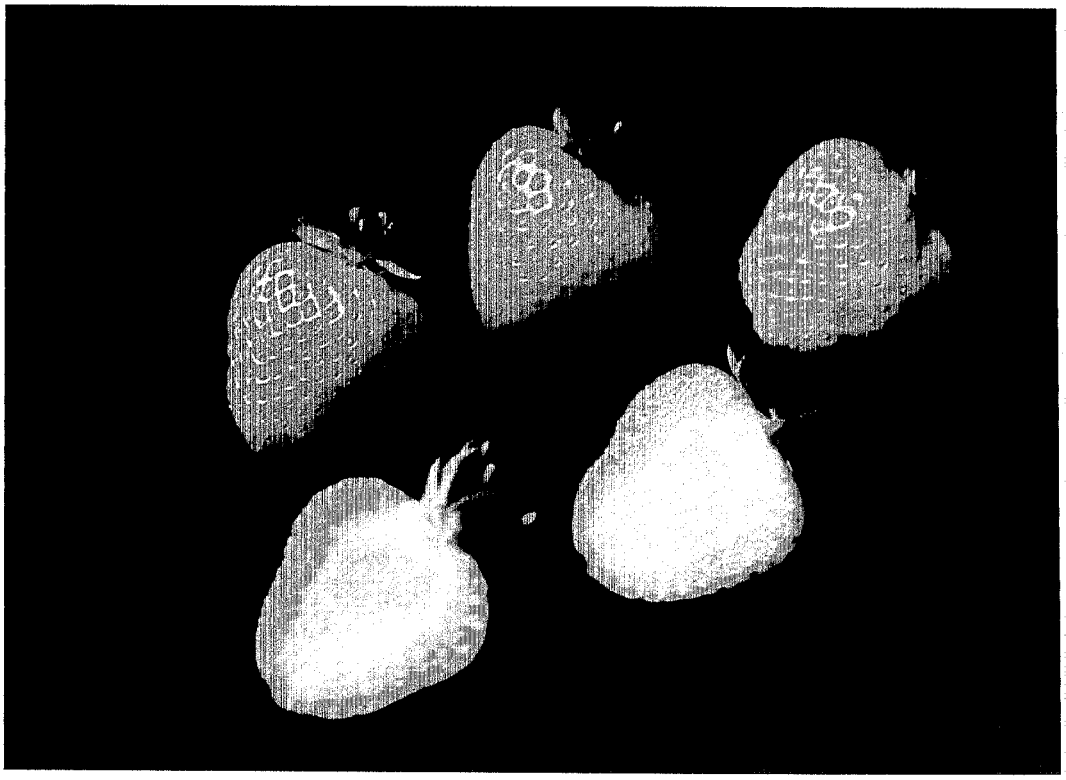
FIG. 4 shows the attractive appearance of the mid-season bright and glossy mature berries of the new Evita variety when whole and when cut in longitudinal cross-sections.

The berries of the new Evita variety are medium to large in size, and possess a configuration that is primarily conical. Also, some wedge-shaped fruits commonly are formed; however, in most instances the wedge is not extremely pronounced. See FIG. 4 in this regard. When grown at South East England, it has been observed that the primary fruits sometimes exhibit severe distortions in shape especially at the commencement of the cropping season. This condition tends to abate as the growing season progresses. The primary fruits commonly measure approximately 4 cm in length×approximately 4 cm in width, the secondary fruits commonly measure approximately 3½ cm in length×approximately 3½ cm in width, and the tertiary fruits commonly measure approximate 3 cm in width×approximately 3 cm in width. The fruit skin is fully colored and an attractive deep orange-red coloration that conveys a bright glossy appearance (as illustrated). The berry skin coloration is dependent upon the degree of maturity and commonly ranges from Orange-Red Group 34A to Red Group 45A at full maturity. The interior flesh coloration when ripe is generally pink. However, when the fruit is not yet ripe, an area of whitening can be observed at the core area of each berry. The interior flesh coloration near the outside fruit surface typically approaches Red-Orange Group 34A, and the interior flesh coloration near the center commonly ranges from approximately Red Group 37A to 37B depending on the maturity.

The achenes are commonly bright yellow and can be tinged with red on the side of the fruit which is not exposed to the sun. The achene coloration commonly is Yellow Group 10A on the shaded side of the fruit, and when fully exposed to the sun the achene coloration commonly is approximately the same as that of the berry skin. The achenes tend to be generally flush with the skin of the berries.

The calyx of the new variety is medium in size and tends to be held away from and clasping the fruit.

The new variety exhibits good flesh firmness; however, such firmness tends to be slightly less than that of Selva and Fern varieties that also exhibit the everbearing character.

The new Evita variety is well suited for fresh fruit consumption, and has been found to exhibit a good taste and to provided a pleasant combination of flavor, sugars and acidity.

We claim:

1. A new and distinct variety of stawberry plant having the following combination of characteristics:

(a) exhibits a semi-erect growth habit, (b) is self-pollinating and tends to bear flowers that are clear of the foliage and which protrude primarly to the sides of the plant, (c) bears leaflets having a slightly-rounded base and slightly-rounded serrations wherein the leaflets commonly tends to be slightly longer in length than in width, and (d) forms on an everbearing basis medium to large attractive berries that exhibit a glossy fully-colored bright orange-red appearance that primarily are conical and sometimes are wedge-shaped in configuration;

substantially as herein shown and described.

* * * * *